(12) United States Patent
Irschik et al.

(10) Patent No.: US 7,947,719 B2
(45) Date of Patent: May 24, 2011

(54) **BIOLOGICALLY ACTIVE COMPOUNDS OBTAINABLE FROM *SORANGIUM CELLULOSUM***

(75) Inventors: Herbert Irschik, Wolfentbüttel (DE); Rolf Jansen, Braunschweig (DE); Florenz Sasse, Braunschweig (DE)

(73) Assignee: Hemholtz-Zentrum fur Infektionsforschung GmbH, Braunschweig (DE)

( * ) Notice: Subject to any disclaimer, the term of this patent is extended or adjusted under 35 U.S.C. 154(b) by 0 days.

(21) Appl. No.: 11/486,140

(22) Filed: Jul. 13, 2006

(65) Prior Publication Data
US 2007/0021480 A1    Jan. 25, 2007

(30) Foreign Application Priority Data
Jul. 15, 2005 (EP) .................................... 05106539

(51) Int. Cl.
C07D 413/00 (2006.01)
A01N 43/76 (2006.01)
A61K 31/42 (2006.01)

(52) U.S. Cl. .......................... 514/374; 548/217; 514/375

(58) Field of Classification Search .................. 548/215, 548/217; 514/374, 375
See application file for complete search history.

(56) References Cited

OTHER PUBLICATIONS

Jin, Zhong, 2006; Natural Product Reports; vol. 23, 464-496.*
Wipf et. al., 2006; Chemical and Biological Drug Design; vol. 67; pp. 66-73.*
Dorwald F. A. Side Reactions in Organic Synthesis, 2005, Wiley: VCH, Weinheim p. IX of Preface.*
Jansen, et. al.; Liebigs Annalen der Chemie (1994), (8), 759-73.*
R. Jansen et al: "Antibiotics from gliding bacteria. LIX. Disorazoles, highly cytoxic metabolites from the sorangicin-producing bacterium Sorangium cellulosum, strain So ce12" Liebigs Annalen Der Chemie, Verlag Chemie GMBH. Weinheim, DE, 1994, pp. 759-773, XP002265587, ISSN: 0170-2041.
R. Jansen, et al: "Chivosazoles A-F: Novel Antifungal and Cytotoxic Macrolides fro Sorangium cellulosum (Myxobacteria)" Liebigs Ann./Recueil 1997 1725-1732.
Yeh, Tetrahedron report 698, Tetrahedrom 60 (2004) 11995-12042.
Wipf, Graham, "Total Synthesis of(-)-Disorazole Cl," J. Am Chem. Soc. 2004, 126, 153456-7.
Hartung et al., "Toward the total synthesis for Disorazole A 1: Asymmetric synthesis of the masked northern half," Synthesis 2003, No. 12, 1844-1850.

Haustedt et al., "Synthetic studies towards the disorazoles: Synthesis of a mask northern half of Disorazole D1 and a cyclopropane analog of the masked northern half of Disorazole A1 ," Tetrahedrom 59 (2003) 6967-6977.
Hillier, Price, Meyers, "Studies on the total synthesis of Disorazole Cl. An advanced macrocycle intermediate," J. Org. Chem. 2001 66,6037-6045, Table 1.
Scudiero, et al, "Evaluation of a Soluble Tetrazolium/Formazan Assay for Cell Growth and Drug Sensitivity in Culture Using Human and Other Tumor Cell Lines," Cancer Research: 48, 4827-4833, Sep. 1, 1988.
Schmidt, et al, "Differential Modulation of paclitaxel-Mediated Apoptosis by $p21^{Waf1}$ and $p27^{Kip1}$," Oncogene (2000) 19, 2423-2429.

* cited by examiner

*Primary Examiner* — Paul V. Ward
(74) *Attorney, Agent, or Firm* — Greer, Burns & Crain Ltd.

(57) ABSTRACT

The present invention relates to a novel group of compounds having antibiotic, antifungal and/or cytostatic properties, which are obtainable from myxobacteria, especially of the genus *Sorangium*, preferably *Sorangium cellulosum*. One representative of this group of compounds is currently named Disorazole Z and Disorazole Z-epoxide, respectively, with specific substituents and specific unsaturated bonds to its cyclic core structure:

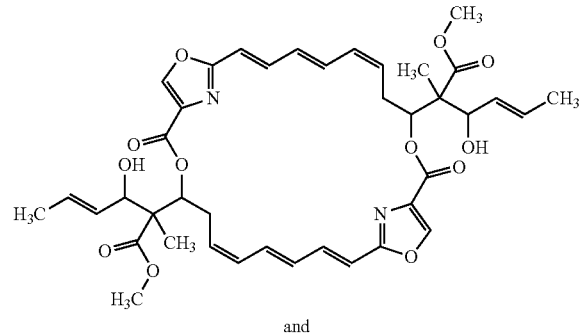

and

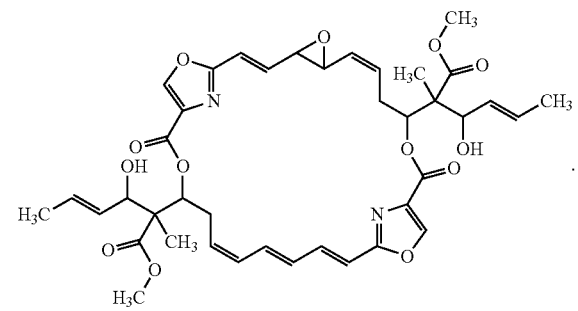

12 Claims, 3 Drawing Sheets

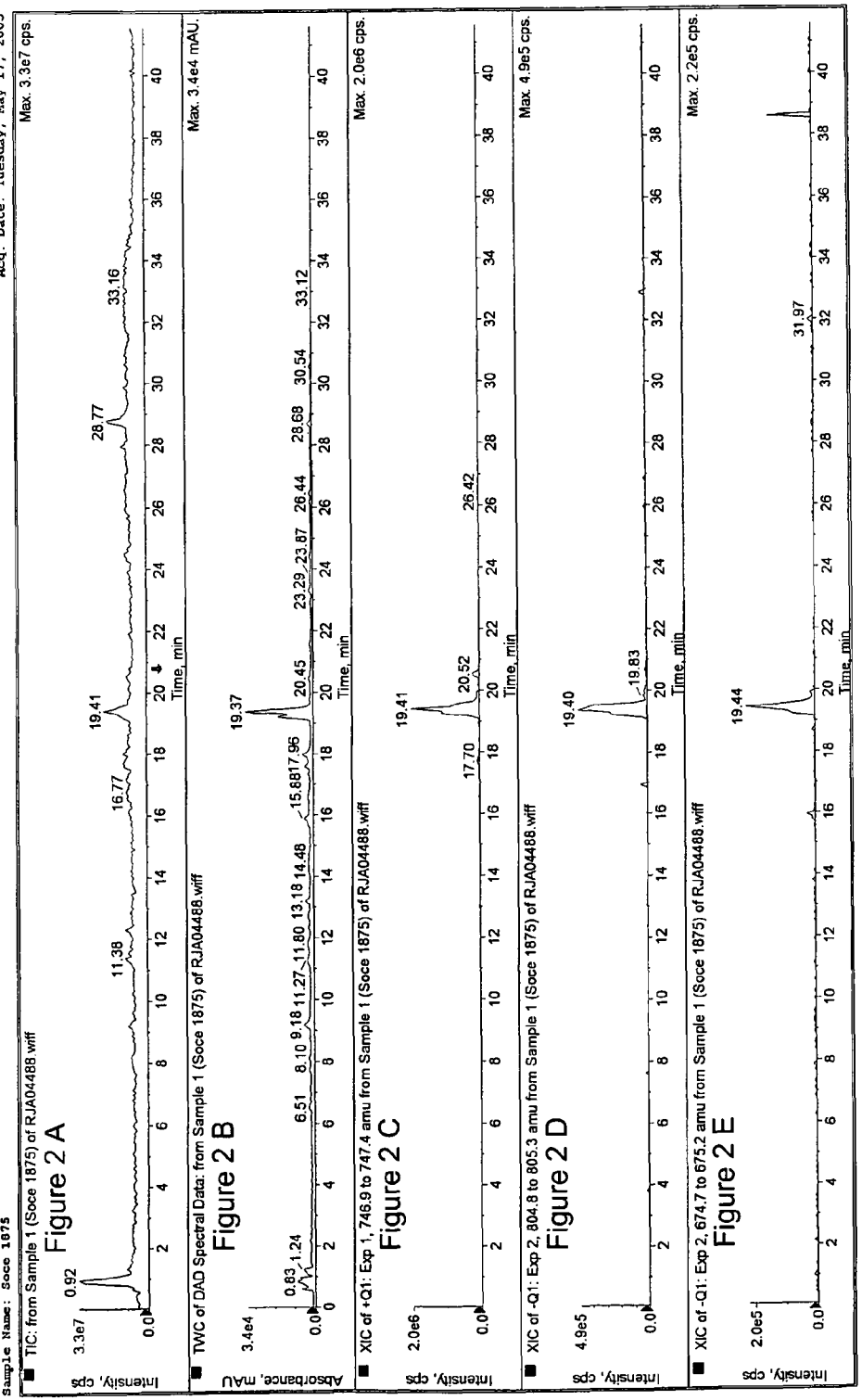

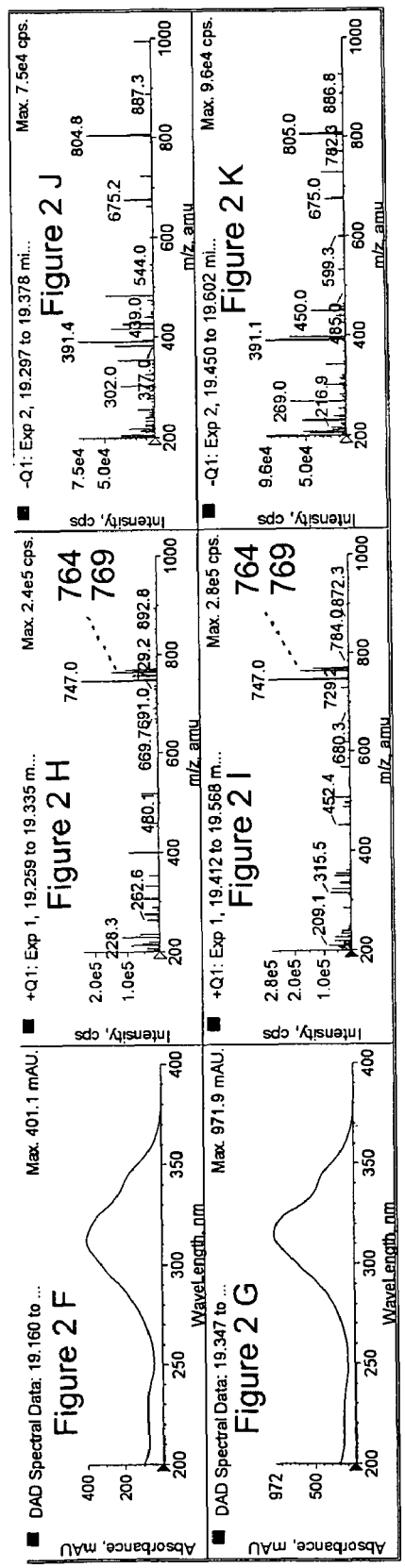

BIOLOGICALLY ACTIVE COMPOUNDS OBTAINABLE FROM *SORANGIUM CELLULOSUM*

CROSS REFERENCE TO RELATED APPLICATIONS

Applicants claim priority under 35 U.S.C. §119 of European Patent No. 05 106 539.9 filed Jul. 15, 2005.

BACKGROUND OF THE INVENTION

1. Field of the Invention

The present invention relates to a novel group of compounds having antibiotic, antifungal and/or cytostatic properties, which are obtainable from myxobacteria, especially of the genus *Sorangium*, preferably *Sorangium cellulosum*. One representative of this group of compounds is currently named Disorazole Z and Disorazole Z-epoxide, respectively, with specific substituents and a specific configuration of unsaturated bonds with its cyclic core structure.

2. Description of Related Art

It is known that myxobacteria produce a large variety of biologically active compounds, which are also termed secondary metabolites. Among these secondary metabolites, the group of Disorazoles has attracted attention as inhibitors for the polymerization of tubulin, for the induction of apoptosis and for the arrest of the cell cycle or inhibition of cell proliferation, even at low concentrations.

Although the compounds of the present invention can be isolated from producer strains of the genus *Sorangium*, they have a substantially differing backbone structure to known Disorazoles or Chivosazoles.

Secondary metabolites isolated from myxobacteria of the genus *Sorangium*, that have been termed Disorazoles can be found in Jansen et al., Liebigs Ann. Chem. 1994, 759-773. One structural formula representative of Disorazoles, termed Disorazole A1 through A7, depending on their substituents, is given below:

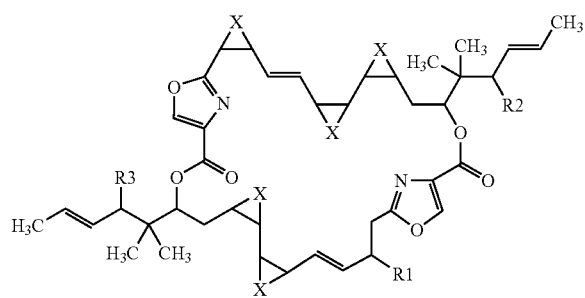

Disorazoles comprise a heterogenous group including two oxazoles in a macrolide ring. In general, Disorazoles have a backbone of a symmetrical circular structure, which can be subdivided into two halves, connected by ester groups, forming a macrolide ring that comprises a total of 34 atoms, part of which carry further substituent groups. Adjacent to one of the ester groups, each of these molecule halves comprises an oxazole ring and a chain of 10 or 12 carbon atoms, followed by an ester group forming the connection to the other molecule half. The chain of 10 to 12 carbon atoms shows a wide range of variations in respect of the arrangement and number of double bonds and further substituents, e.g. epoxy groups, hydroxyl groups and further substituent saturated or partially unsaturated alkyl groups.

Another group of secondary metabolites obtainable from myxobacteria, especially *Sorangium cellulosum* is termed Chivosazoles, the backbone structure of which is given below as identified by Jansen et al. (Liebigs Ann./Recueil 1997, 1725-1732 (1997)). In general, Chivosazoles can be described as glycosides of 6-deoxyglucopyranose derivatives of an aglycon which includes an oxazole in its 31-membered macrolide ring. The aglycon itself is termed Chivosazole F, showing antibiotic and cytotoxic activities:

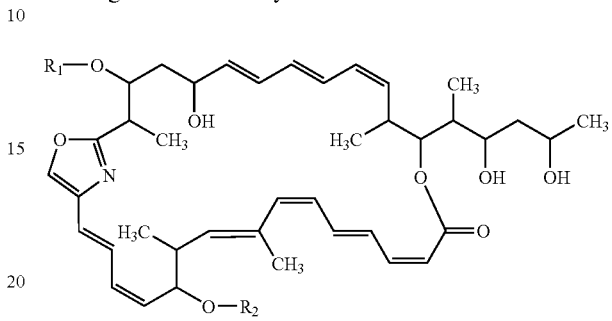

Above: Chivosazole aglycon (F), wherein $R_1$ is H or —$CH_3$. Substituents for $R_2$ are termed chinovosyl derivatives.

SUMMARY OF THE INVENTION

In view of known secondary metabolites obtainable from myxobacteria of the genus *Sorangium*, it is an object of the present invention to provide novel compounds having biological activities, e.g. antifungal, antibiotic and/or cytotoxic properties.

In order to achieve the above-mentioned objects, the present invention provides a novel compound having biological activitiy, its use for medical purposes, and pharmaceutical compositions comprising the compound. Further, the present invention provides a process for production of the compound by fermentation of micro-organisms.

The compound of the present invention comprises a cyclic core structure according to formula I, which is comprised in or forms part of a biologically active compound, wherein any single or all of the bonds between carbon atoms C5 to C12 and any of the bonds between C5' and C12' may each singly or all be saturated or unsaturated, independently from each other, in cis- or trans-configuration, preferably conjugatedly unsaturated:

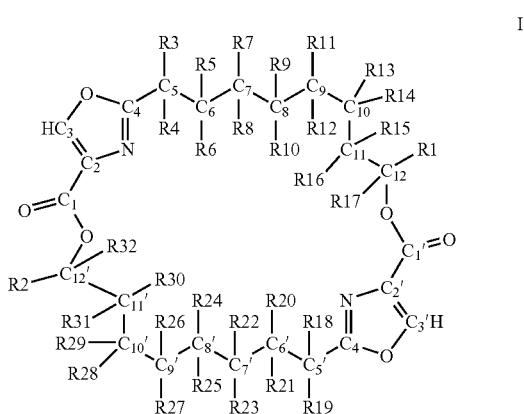

wherein substituents R1 to R32 are independently selected from the group consisting of hydrogen, alkyl, cycloalkyl, cycloalkylalkyl, alkenyl, alkynyl, aryl, heteroaryl, arylalkyl, heteroarylalkyl, heterocyclyl, heterocyclylalkyl, alkylsulfonyl, arylsulfonyl, arylalkylsulfonyl, halogen, hydroxyl, carbonyl, acetyl, alkoxyl, aryloxyl, arylalkyloxyl, amino, imino, hydroxylamino, mono-alkylamino, di-alkylamino, hydrazinyl, cyano, alkylcyano, sulfhydryl, disulfidylalkyl, sulfatidyl, and alkylsulfidyl.

Optionally, substituents R1 to R32 are further substituted in their alkyl, cycloalkyl, cycloalkylalkyl, alkenyl, alkynyl, aryl, heteroaryl, arylalkyl, heteroarylalkyl, heterocyclyl, heterocyclylalkyl, alkylsulfonyl, arylsulfonyl, arylalkylsulfonyl, carbonyl, acetyl, alkoxyl, aryloxyl, arylalkyloxyl, mono-alkylamino, di-alkylamino, alkylcyano, disulfidylalkyl, and/or alkylsulfidyl groups by 1, 2 or 3 substituents independently selected from the group consisting of alkyl, cycloalkyl, cycloalkylalkyl, alkenyl, alkynyl, aryl, heteroaryl, arylalkyl, heteroarylalkyl, heterocyclyl, heterocyclylalkyl, alkylsulfonyl, arylsulfonyl, arylalkylsulfonyl, halogen, fluoro, chloro, bromo, iodo, —N$_3$, NO$_2$, =O, =S, =S(O)$_2$, hydroxyl, carbonyl, acetyl, alkoxyl, aryloxyl, arylalkyloxyl, amino, imino, hydroxylamino, mono-alkylamino, di-alkylamino, hydrazinyl, cyano, alkylcyano, sulfhydryl, disulfidylalkyl, sulfatidyl and alkylsulfidyl.

Additionally or alternatively, any two substituents R1 to R32, bound to neighbouring carbon atoms selected from C1 to C12 and C1' to C12', respectively, can be a double bond, an epoxide(oxiran), an aziran(aziridine), alkyl-, alkenyl-, alkynyl-, cycloalkyl-, cycloalkylalkyl, heteroaryl-, arylalkyl-, heteroarylalkyl-, heterocyclyl-, and/or heterocyclylalkyl-substituted aziran(aziridine), thiirane and/or a thiirane-S-oxide group between two neighbouring carbon atoms, preferably selected from C5 to C12 and from C5' to C12', respectively. Preferably, bonds between carbon atoms C5 to C12 and between C5' to C12', respectively, are conjugatedly unsaturated. More preferably, bonds between carbon atoms C5 and C6, between C7 and C8, and between C9 and C10 as well as bonds between carbon atoms C5' and C6', between C7' and C8', and between C9' and C10' are unsaturated. Asymmetrical carbon atoms are R- or S-configured, preferably having the configuration of products obtainable from *Sorangium*.

Preferably, bonds between carbon atoms C1 to C12 and C1' to C12', respectively, are unsaturated according to structure II, wherein carbon atoms C5 to C12 and C5' to C12' carry substituents R3 to R17 and R18 to R32, respectively, which are not shown but correspond to those of structure I.

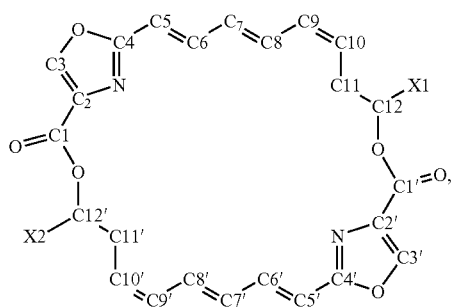

II wherein carbon atoms C5 to C11 and C5' to C11' are substituted according to structure I, namely C5 with R4, C6 with R6, C7 with R8, C8 with R10, C9 with R12, C10 with R14 and C11 with R16, C5' with R18, C6' with R20, C7' with R22, C8' with R24, C9' with R26, C10' with R28, and C11' with R30, and wherein X1 and X2 are independently selected from groups defined for substituents R1 to R32 or as defined for substituents X1 below.

In a further embodiment, general structure I carries a substituted ethyl group on carbon atoms C12 and C12', respectively, resulting in the following structure III:

III

Substituents R33 to R70 are independently selected from the group consisting of hydrogen, alkyl, cycloalkyl, cycloalkylalkyl, alkenyl, alkynyl, aryl, heteroaryl, arylalkyl, heteroarylalkyl, heterocyclyl, heterocyclylalkyl, alkylsulfonyl, arylsulfonyl, arylalkylsulfonyl, halogen, hydroxyl, carbonyl, acetyl, alkoxyl, aryloxyl, arylalkyloxyl, amino, imino, hydroxylamino, mono-alkylamino, di-alkylamino, hydrazinyl, cyano, alkylcyano, sulfhydryl, disulfidylalkyl, sulfatidyl, and alkylsulfidyl.

Optionally, substituents R33 to R70 are further substituted in their alkyl, cycloalkyl, cycloalkylalkyl, alkenyl, alkynyl, aryl, heteroaryl, arylalkyl, heteroarylalkyl, heterocyclyl, heterocyclylalkyl, alkylsulfonyl, arylsulfonyl, arylalkylsulfonyl, carbonyl, acetyl, alkoxyl, aryloxyl, arylalkyloxyl, mono-alkylamino, di-alkylamino, alkylcyano, disulfidylalkyl, and/or alkylsulfidyl groups by 1, 2 or 3 substituents independently selected from the group consisting of alkyl, cycloalkyl, cycloalkylalkyl, alkenyl, alkynyl, aryl, heteroaryl, arylalkyl, heteroarylalkyl, heterocyclyl, heterocyclylalkyl, alkylsulfonyl, arylsulfonyl, arylalkylsulfonyl, halogen, fluoro, chloro, bromo, iodo, —N$_3$, NO$_2$, =O, =S, =S(O)$_2$, hydroxyl, carbonyl, acetyl, alkoxyl, aryloxyl, arylalkyloxyl, amino, imino, hydroxylamino, mono-alkylamino, di-alkylamino, hydrazinyl, cyano, alkylcyano, sulfhydryl, disulfidylalkyl, sulfatidyl and alkylsulfidyl.

Additionally or alternatively, any two substituents R33 to R70, bound to neighbouring carbon atoms selected from C1 to C12 and C1' to C12', respectively, can be a double bond, an epoxide(oxiran), an aziran(aziridine), alkyl-, alkenyl-, alkynyl-, cycloalkyl-, cycloalkylalkyl, heteroaryl-, arylalkyl-, heteroarylalkyl-, heterocyclyl-, and/or heterocyclylalkyl-substituted aziran(aziridine), thiirane and/or a thiirane-S-oxide group between two neighbouring carbon atoms, preferably selected from C5 to C12 and from C5' to C12', respectively.

Preferably, bonds between carbon atoms C5 to C12 and between C5' to C12', respectively, are conjugatedly unsaturated. More preferably, bonds between carbon atoms C5 and C6, between C7 and C8, and between C9 and C10 as well as bonds between carbon atoms C5' and C6', between C7' and C8', and between C9' and C10' are unsaturated. Asymmetrical carbon atoms are R- or S-configured, preferably having the configuration of products obtainable from *Sorangium*.

Preferably, bonds between carbon atoms C1 to C14 and C1' to C14', respectively, are unsaturated according to structure IV, wherein substituents to carbon atoms C5 to C12 and to carbon atoms C5' to C12' are not shown but are identical to R42 to R70 as defined for structure II. Substituents X3, X4, X5, X6, X7, and X8 also correspond to R33 to R39 of structure III.

heteroarylalkyl, heterocyclyl, heterocyclylalkyl, alkylsulfonyl, arylsulfonyl, arylalkylsulfonyl, halogen, fluoro, chloro, bromo, iodo, —N$_3$, NO$_2$, =O, =S, =S(O)$_2$, hydroxyl, carbonyl, acetyl, alkoxyl, aryloxyl, arylalkyloxyl, amino, imino, hydroxylamino, mono-alkylamino, di-alkylamino, hydrazinyl, cyano, alkylcyano, sulfhydryl, disulfidylalkyl, sulfatidyl and alkylsulfidyl.

IV

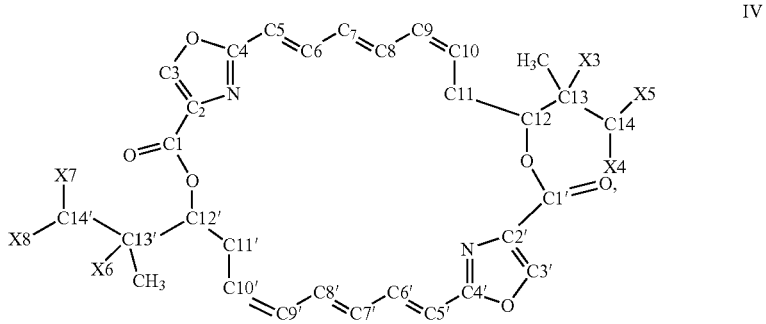

In a further preferred embodiment of the invention, at least two carbon atoms of C5 to C12 and/or of C5' to C12' in structures according to formulae I, II or III are bridged by an epoxy group. As an example for an epoxide containing compound of the invention, the following structure V is given, wherein double bonds can be formed between carbon atoms C5 to C12 and C5' to C12':

V

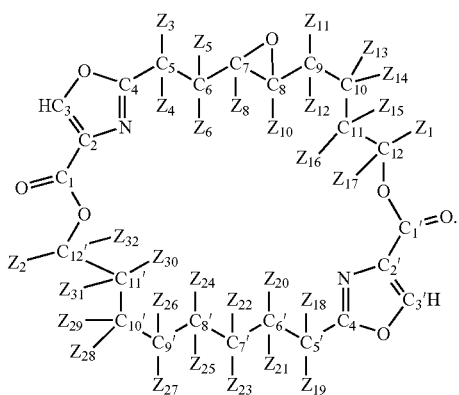

Substituents Z1 to Z32 are independently selected from the group consisting of hydrogen, alkyl, cycloalkyl, cycloalkylalkyl, alkenyl, alkynyl, aryl, heteroaryl, arylalkyl, heteroarylalkyl, heterocyclyl, heterocyclylalkyl, alkylsulfonyl, arylsulfonyl, arylalkylsulfonyl, halogen, hydroxyl, carbonyl, acetyl, alkoxyl, aryloxyl, arylalkyloxyl, amino, imino, hydroxylamino, mono-alkylamino, di-alkylamino, hydrazinyl, cyano, alkylcyano, sulfhydryl, disulfidylalkyl, sulfatidyl, and alkylsulfidyl.

Optionally, substituents Z1 to Z32 are further substituted in their alkyl, cycloalkyl, cycloalkylalkyl, alkenyl, alkynyl, aryl, heteroaryl, arylalkyl, heteroarylalkyl, heterocyclyl, heterocyclylalkyl, alkylsulfonyl, arylsulfonyl, arylalkylsulfonyl, carbonyl, acetyl, alkoxyl, aryloxyl, arylalkyloxyl, mono-alkylamino, di-alkylamino, alkylcyano, disulfidylalkyl, and/or alkylsulfidyl groups by 1, 2 or 3 substituents independently selected from the group consisting of alkyl, cycloalkyl, cycloalkylalkyl, alkenyl, alkynyl, aryl, heteroaryl, arylalkyl, Additionally or alternatively, any two substituents Z1 to Z32, bound to neighbouring carbon atoms selected from C1 to C12 and C1' to C12', respectively, can be a double bond, an epoxide(oxiran), an aziran(aziridine), alkyl-, alkenyl-, alkynyl-, cycloalkyl-, cycloalkylalkyl, heteroaryl-, arylalkyl-, heteroarylalkyl-, heterocyclyl-, and/or heterocyclylalkyl-substituted aziran(aziridine), thiirane and/or a thiirane-S-oxide group between two neighbouring carbon atoms, preferably selected from C5 to C12 and from C5' to C12', respectively.

Preferably, bonds between carbon atoms C5 to C12 and between C5' to C12', respectively, are conjugatedly unsaturated. More preferably, bonds between carbon atoms C5 and C6, between C7 and C8, and between C9 and C10 as well as bonds between carbon atoms C5' and C6', between C7' and C8', and between C9' and C10' are unsaturated. Asymmetrical carbon atoms are R- or S-configured, preferably having the configuration of products obtainable from *Sorangium*.

Preferably, bonds between carbon atoms C1 to C12 and C1' to C12', respectively, are unsaturated according to following structure VI, wherein substituents to carbon atoms C5 to C12 and to carbon atoms C5' to C12' are not shown but are as defined for structure V.

IV

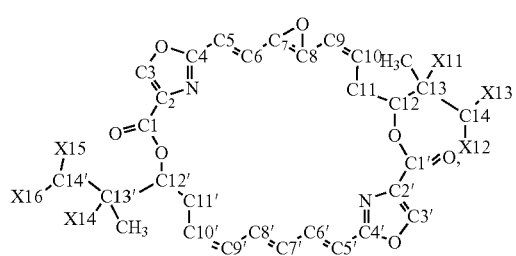

wherein substituents X11 to X16 are selected from the groups defined for R1 to R32.

Further, structure V can be isolated from fermentation broth of *Sorangium*, synthesized or obtained by derivatization to obtain compounds according to the following structure VII, wherein substituents Z33 to Z70 are identical to substituents Z1 to Z32:

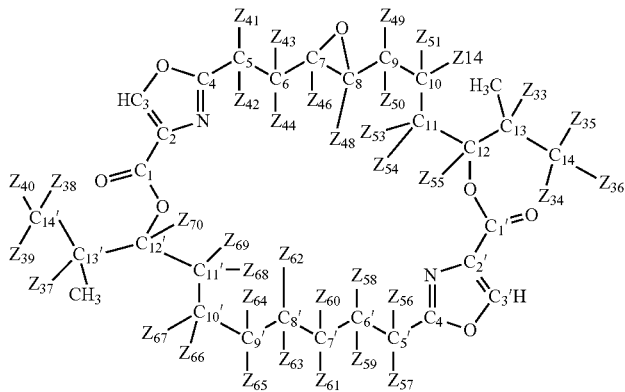

VII

A specific embodiment of the epoxide according to structures VI and VII is given in following structure VIII that is also obtainable from producer strains of the genus *Sorangium*:

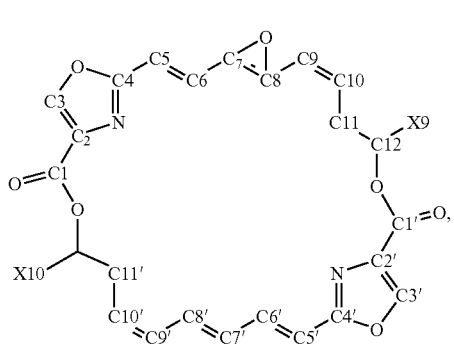

VIII wherein substituents X9 and X10 are defined as given for substituents Z1 to Z32.

In the structures of formula I to VIII, double bonds are independently in cis- or trans-configuration.

In a further preferred embodiment of the above structures, one or both of the lactonizing bonds, which according to formulae I to VIII are formed between C12 and C1' and between C12' and C1, respectively, may instead be formed between C14 and C1' and/or C14' and C1, respectively, formally replacing one of the substituents of C14 and C14', respectively.

It is noticeable that all of the compounds according to the invention can be isolated from fermentation broth of *Sorangium*, especially of *Sorangium cellulosum*, because synthesis of theses secondary metabolites varies over the duration of the fermentation. For example, the variation of cis-/trans-configuration of double bonds between C5 and C14 or C5' and C14' as well as their conjugation and/or state of saturation and/or formation of the lactonizing bond between C14 to C1' instead of between C12 and C1' and/or between C14' and C1 instead of between C12' and C1 differ with longer fermentation times, e.g. extended to 15 or 20 days. Further, alteration of the fermentation conditions, e.g. by omitting the adsorbing resin XAD amberlite from the culture medium results in synthesis of compounds having structures according to formulae I to IV, e.g. products having different substituents to their carbon atoms as well as variations in the desaturation of bonds between C5 to C12 and C5' to C12', and in relation to the positioning of the lactonizing bond.

The synthesis of compounds having the same core structure, presently of formulae I to VIII, with different substitutents to C1 to C14 and C1' to C14' and different saturation/unsaturation and different conformation of bonds in fermentation by *Sorangium* corresponds to the observations made by Jansen et al. (Liebigs Ann. Chem. 1994, 759-773) in respect of the large number of variants of dizorazoles. As an alternative to isolation from fermentation broth of *Sorangium*, compounds of the invention can be obtained by total chemical synthesis or by derivatization of Disorazole Z or of its epoxide, both obtainable by fermentation. As the present invention provides the structures of compounds, chemical routes for synthesis can be devised by a skilled person using generally known methods of synthetic chemistry.

In a preferred embodiment, substituents R1, R2, X1, X2, X9, X10, Z1 and Z2 of the above formulae I to VIII are independently selected from the following substituent groups:

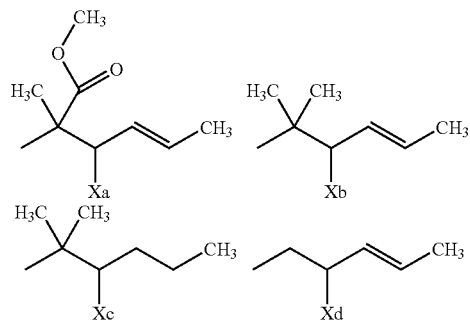

In the above formulae, Xa, Xb, Xc and Xd may be selected independently from the following atoms or groups: Hydrogen, alkyl, cycloalkyl, cycloalkylalkyl, alkenyl, alkynyl, aryl, heteroaryl, arylalkyl and heteroarylalkyl, heterocyclyl, heterocyclylaryl, alkylsulfonyl, arylsulfonyl and arylalkylsulfonyl, halogen, hydroxyl, carbonyl, acetyl and alkoxyl, amino, imino, hydroxylamino, monoalkylamino, dialkylamino, hydrazinyl, cyano, alkylcyano, sulfhydryl, disulfidylalkyl, sulfatidyl, alkylsulfidyl, aryloxyl, arylalkyloxyl, =O, =S, =S(O)$_2$, which are optionally substituted in the alkyl, cycloalkyl, cycloalkylalkyl, alkenyl, alkynyl, aryl, heteroaryl, arylalkyl, heteroarylalkyl, heterocyclyl, heterocyclylalkyl, alkylsulfonyl, arylsulfonyl, arylalkylsulfonyl, carbonyl, acetyl, alkoxyl, aryloxyl, arylalkyloxyl, mono-alkylamino, di-alkylamino, alkylcyano, disulfidylalkyl and/or alkylsulfidyl group by 1, 2 or 3 substituents independently from each other selected from the group consisting of alkyl, cycloalkyl, cycloalkylalkyl, alkenyl, alkynyl, aryl, heteroaryl, arylalkyl, heteroarylalkyl, heterocyclyl, heterocyclylalkyl, alkylsulfonyl, arylsulfonyl, arylalkylsulfonyl, halogen, e.g. fluoro, chloro, bromo, iodo, $-N_3$, $-NO_2$, $=O$, $=S$, $=S(O)_2$, hydroxyl, carbonyl, acetyl, alkoxyl, aryloxyl, arylalkyloxyl, amino, imino, hydroxylamino, mono-alkylamino, di-alkylamino, hydrazinyl, cyano, alkylcyano, sulfhydryl, disulfidylalkyl, sulfatidyl and/or alkylsulfidyl.

More preferably, substituents R1, R2, X1, X2, X9, X10, Z1, Z2 are selected from the following substituent groups:

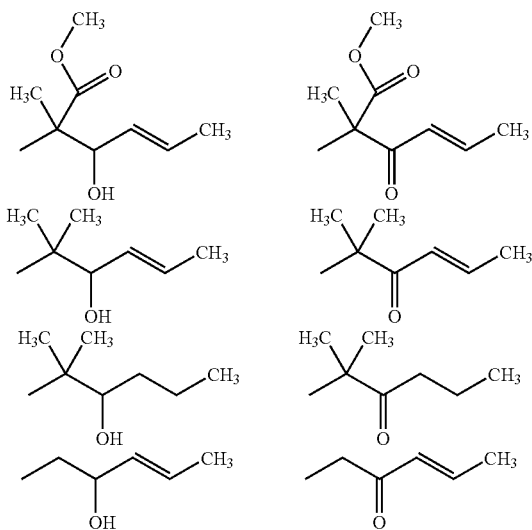

Most preferably, the substituents R1, R2, X1, X2, X9, X10, Z1, Z2 are identical within one compound.

The term alkyl for the purposes of this invention includes acyclic saturated hydrocarbons having 1 to 12 carbon atoms, which alkyls may be linear or branched. The term alkyl preferably stands for alkyl chains of 1 to 8, particularly preferable 1 to 6 carbon atoms. Examples of suitable alkyl radicals are methyl, ethyl, n-propyl, isopropyl, n-butyl, isobutyl, sec.-butyl, tert.-butyl, n-pentyl, tert.-pentyl, 2- or 3-methyl-pentyl, n-hexyl, isohexyl, n-heptyl, n-octyl, n-nonyl, n-decyl, n-undecyl, n-dodecyl.

The term cycloalkyl represents saturated or partially unsaturated non-aromatic cyclic hydrocarbon groups or radicals, containing 1 to 3 rings, including monocyclic alkyl, bicyclic alkyl, tricyclic alkyl, and containing a total of 3 to 20 carbon atoms forming the rings, preferably 3 to 10 carbon atoms, most preferably cycloalkyl having 3 to 8 carbon atoms. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl, and cyclooctadienyl.

The term cycloalkylalkyl refers to a radical in which the cycloalkyl group is linked via an alkyl group, where alkyl and cycloalkyl groups have the meanings defined herein, preferably a $(C_3-C_8)$-cycloalkyl-$(C_1-C_4)$-alkyl radical. Examples thereof are cyclopropylmethyl, cyclohexylmethyl, cyclopentylethyl, cyclohexenylethyl.

The term alkenyl for the purposes of this invention includes cyclic unsaturated or partially unsaturated hydrocarbons having from 2 to 12 carbon atoms, which may be linear or branched and may contain 1 or more double bonds. The term alkenyl preferably stands for alkenyl chains having 2 to 8, preferably 2 to 6 carbon atoms. Examples are vinyl, propenyl, butenyl, pentenyl, hexenyl, and octadienyl and the like.

The term alkynyl refers to cyclic unsaturated or partially unsaturated hydrocarbons having from 2 to 12 carbon atoms, which may be straight-chain or branched and contain 1 or more triple bonds. The term alkenyl preferably stands for alkenyl chains having 2 to 8, preferably 2 to 6 carbon atoms. Examples are propynyl, butynyl, pentynyl, hexynyl.

The term aryl refers to aromatic hydrocarbon systems having 3 to 14, preferably 5 to 14, carbon atoms, which may also be fused to further saturated, (partially) unsaturated or aromatic cyclic systems. Examples of aryl are inter alia phenyl, biphenyl, naphthyl and anthracenyl, but also indanyl, indenyl, or 1,2,3,4-tetrahydronaphtyl.

The term heteroaryl refers to a 5-, 6- or 7-membered cyclic aromatic radical which comprises at least 1, where appropriate also 2, 3, 4, or 5 heteroatoms, preferably nitrogen, oxygen and/or sulfur, wherein the heteroatoms are identical or different. The number of nitrogen atoms independently is preferably 0, 1, 2 or 3, and that of the oxygen and sulfur atoms independently is 0 or 1. The term heteroaryl also includes systems in which the aromatic cycle is part of a bi- or polycyclic system, such as were the aromatic cycle is fused to an aryl, cycloalkyl, heteroaryl or heterocyclyl group as defined herein via any desired and possible ring member of the heteroaryl radical. Examples of heteroaryl include pyrrolyl, thienyl, furyl, imidazolyl, thiazolyl, isothiazolyl, oxazolyl, isoxazolyl, pyrazolyl, pyridinyl, pyrimidinyl, pyrazinyl, indolyl, quinolinyl, and isoquinolinyl.

The terms arylalkyl and heteroarylalkyl refer to radicals in which the aryl or heteroaryl radical is linked via an alkyl group, where the alkyl, aryl and heteroaryl groups have the meanings defined herein. Preferred arylalkyl groups are phenyl-$(C_1-C_4)$-alkyl radicals, preferably benzyl or phenylethyl radicals. Preferred heteroarylalkyl groups are indolyl-$(C_1-C_4)$-alkyl radicals, preferably 1H-indole-3-yl-methyl or 2 (1H-indole-3-yl)-ethyl.

The term heterocyclyl refers to a mono- or polycyclic system of 3 to 14, preferably 5 or 6 to 14 ring atoms which may be exclusively carbon atoms. However, the cyclic system may also comprise 1, 2, 3, 4, or 5 heteroatoms, in particular nitrogen, oxygen and/or sulfur. The cyclic system may be saturated, mono- or polyunsaturated but may not be aromatic. In the case of a cyclic system consisting of at least two rings, these rings may be fused or spiro- or otherwise connected. The heterocyclyl radical may be attached at any carbon or heteroatom which results in the creation of a stable structure. Examples include pyrrolidinyl, thiapyrrolidinyl, piperidinyl, piperazinyl, oxapiperazinyl, oxapiperidinyl and oxadiazolyl.

The term heterocyclylalkyl refers to radicals in which the heterocyclyl group is linked via an alkyl group, where the alkyl and heterocyclyl groups have the meanings defined herein.

The terms alkylsulfonyl, arylsulfonyl and arylalkylsulfonyl refer to radicals in which the alkyl, aryl or arylalkyl group is linked via a $-S(O_2)$-group, where the alkyl, aryl and arylalkyl groups have the meanings defined herein. Examples are methylsulfonyl and phenylsulfonyl.

The term halogen refers to one, where appropriate a plurality of fluorine (F, fluoro), bromine (Br, bromo), chlorine (Cl, chloro), or iodine (I, iodo) atoms. Halogen preferably means a fluorine, chlorine or bromine atom.

The terms alkoxyl, aryloxyl, and arylalkyloxyl refer to radicals in which an alkyl, aryl or arylalkyl chain, respectively, as defined herein is linked via an oxygen atom. Examples are methoxyl, n-propyloxyl, phenyloxyl, and benzyloxyl.

The term mono(di)-alkylamino refers to radicals in which up to one (two) independent alkyl chain(s) as defined herein is (are) linked via a nitrogen atom. Examples are ethylamino, dimethylamino and isopropylethylamino.

The term alkylcyano refers to radicals in which an alkyl chain as defined herein is linked via a cyano group. Examples are methylcyano and n-propylcyano.

The term alkylsulfidyl refers to radicals in which an alkyl chain as defined herein is linked via a sulfur atom. Examples are methylsulfidyl and n-propylsulfidyl.

The term carbonyl refers to radicals in which an alkyl, cycloalkyl, cyloalkylalkyl, alkenyl, alkynyl, aryl, heteroaryl, arylalkyl, heteroarylalkyl, heterocyclyl and/or heterocyclylalkyl group is linked by a —C(O)— or a —C(O)O—group, with the terms alkyl, cycloalkyl, cyloalkylalkyl, alkenyl, alkynyl, aryl, heteroaryl, arylalkyl, heteroarylalkyl, heterocyclyl and/or heterocyclylalkyl as defined herein. Examples are —C(O)O—CH$_3$, —C(O)—CH$_3$, —C(O)O-phenyl and the like.

All stereoisomers of the compounds of the invention are contemplated, either in a mixture or in pure or substantially pure form. The compounds of the present invention can have asymetric centers at any of the carbon atoms including any one of the R substituents. Consequently, compounds of the invention can exist in the form of their racemates, in the form of the pure enantiomers and/or diastereomers or in the form of mixtures of these enantiomers and/or diastereomers. The mixtures may have any desired mixing ratio of the stereoisomers.

Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or nonchiral phases or by recrystallization from an optionally optically active solvent or with use of an optically active acid or base or by derivatization with an optically active reagent such as, for example, an optically active alcohol, and subsequent elimination of the radical.

Where possible, the compounds of the invention may be in the form of the tautomers.

It is likewise possible for the compounds of the invention to be in the form of prodrugs like acetates, carbonates, glucoronates, sulfates, or phosphates. According to the invention pharmaceutical compositions can comprise an inert nontoxic pharmaceutical carrier and at least one compound of the invention.

The compounds of the invention can, if they have a sufficiently basic group such as, for example, a secondary or tertiary amino, be converted with inorganic and organic acids into salts. The pharmaceutically acceptable salts of the compounds of the invention are preferably formed with hydrochloric acid, hydrobromic acid, iodic acid, sulfuric acid, phosphoric acid, methanesulfonic acid, p-toluenesulfonic acid, carbonic acid, formic acid, acetic acid, sulfoacetic acid, trifluoroacetic acid, oxalic acid, malonic acid, maleic acid, succinic acid, tartaric acid, racemic acid, malic acid embonic acid, mandelic acid, fumaric acid, lactic acid, citric acid, taurocholic acid, glutaric acid, stearic acid, glutamic acid or aspartic acid. The salts which are formed are, inter alia, hydrochlorides, chlorides, hydrobromides, bromides, iodides, sulfates, phosphates, methanesulfonates, tosylates, carbonates, bicarbonates, formats, acetates, sulfoacetates, triflates, oxalates, malonates, maleates, succinates, tartrates, malates, embonates, mandelates, fumarates, lactates, citrates, taurocholates, glutarates, stearates, glutaminates and aspartates, respectively.

The stochiometry of salts formed form the compounds of the invention may moreover be an integral or non-integral multiple of one. The compounds of the invention can, if containing a sufficiently acidic group, e.g. a carboxy, sulfonic acid, phosphoric acid or phenolic group, be converted with inorganic bases into their physiologically acceptable salts. Examples for inorganic bases are ammonium, sodium hydroxide, potassium hydroxide, calcium hydroxide, suitable organic bases are ethanolamine, diethanolamine, triethanolamine, ethylenediamine, t-butylamine, t-octylamine, dehydroabietylamine, cyclohexylamine, dibenzylethylene-diamine and lysine.

It is likewise possible for the compounds of the invention to be in the form of their solvates and, in particular, hydrates that can be obtained e.g. by crystallization form a solvent or an aqueous solution. Further, it is possible for one, two, three or any number of solvate or water molecules to combine with the compounds of the invention to give solvates and hydrates.

It is known that chemical substances form solids that exist in different order states, referred to as polymorphic forms or modifications. The various modifications of a polymorphic substance may differ greatly in their physical properties. The compounds of the invention can exist in various polymorphic forms, of which certain modifications may moreover be metastable. All of these polymorphic forms of the compounds of the invention are regarded as being embraced by the scope of the invention.

More preferred, X1 and X2 of structure II are identical substituent groups, resulting in the following structure IX, which compound is presently termed Disorazole Z:

IX

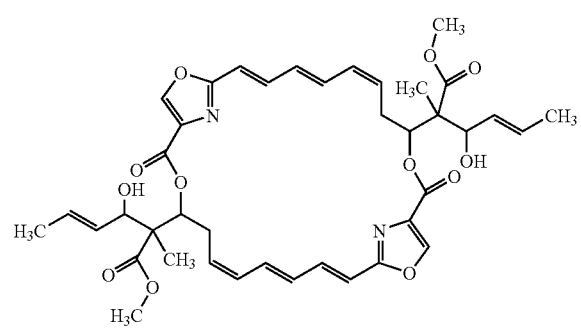

For the Disorazole Z-epoxide, a molecular formula of $C_{40}H_{46}N_2O_{13}$ giving a formula weight of 762.79884 and a monoisotopic mass of 762.29999 Da were determined, from which a structure according to formula X was deduced:

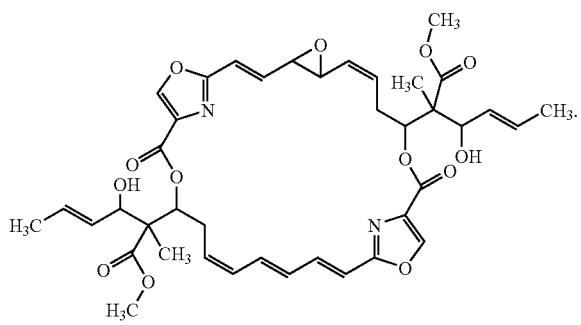

In the novel compounds according to the above formulae I to X, the asymmetrical carbon atoms may each be present in the R- or S-configuration, preferably in the configuration as synthesized by a producer strain of the genus *Sorangium*. However, a person skilled in the art is capable of determining the configuration which is present in the biosynthetic product of *Sorangium* and, further, determining the biological activities of each stereoisomer.

For production of the novel compound, chemical synthesis according to standard procedures known to the person skilled in the art can be employed and, preferably, fermentation of a myxobacterial strain is carried out, preferably of the genus *Sorangium*, which is a producer strain of the compound, followed by isolation and purification procedures. Compounds according to the present invention are suitable for medical use, i.e. as components of pharmaceutical preparations, for example for the treatment of chronic inflammatory diseases, e.g. arthritis, or as drugs or pro-drugs effective against tumor cells.

Apart from providing a novel cyclic core structure as a basis for biologically active compounds, one of the advantages of compounds according to the present invention, e.g. over known Disorazoles is their improved long-term stability, e.g. in solid preparations or in liquid formulations.

With respect to the asymmetrical epoxy group contained in compounds according to the second embodiment, the reactive epoxy group may advantageously be used both for further derivatizations of the compound or for providing a differing and/or enhanced biological activity.

BRIEF DESCRIPTION OF THE DRAWINGS

FIGS. 2A to K show analytical results for Disorazole Z obtained by HPLC-MS HPLC chromatography, UV-spectrometry and mass spectrometry, respectively, for an extract from a fermentation of *Sorangium cellulosum*.

DETAILED DESCRIPTION OF PREFERRED EMBODIMENTS

Figure 1:
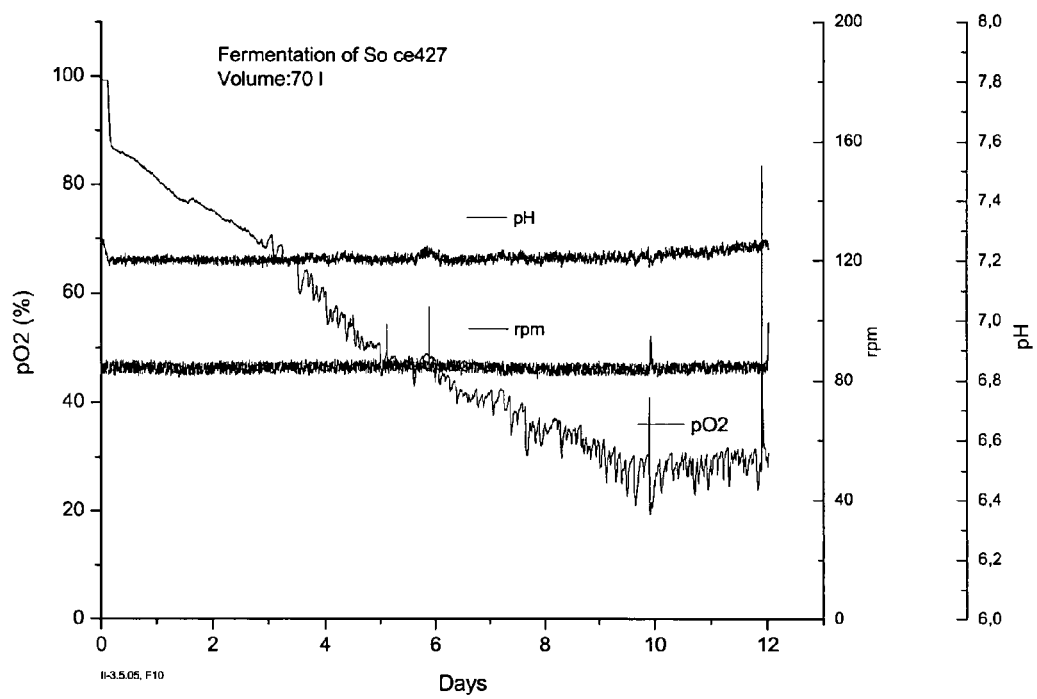
FIG. 1 shows the course of oxygen saturation, pH and stirrer speed of a typical fermentation of *Sorangium cellulosum*.

The present invention is now described in greater detail with reference to the figures, wherein FIG. 1 shows the course of oxygen saturation, pH and stirrer speed of a typical fermentation of *Sorangium cellulosum*, and FIGS. 2A to H show analytical results for Disorazole Z obtained by HPLC-MS HPLC chromatography, UV-spectrometry and mass spectrometry, respectively, for an extract from a fermentation of *Sorangium cellulosum*, namely in detail in FIG. 2A the total ion current chromatogram (TIC) 200-1000 Da, in FIG. 2B the DAD-UV chromatogram in the range of 200-400 nm, in FIG. 2C the extracted positive ion current (XIC) chromatogram adjusted to the M+H ion of Disorazole Z and Z-isomers (746.9-747.4 Da), in FIG. 2D the extracted negative ion current (XIC) chromatogram adjusted to the M−H+AcOH ion of Disorazole Z and Z-isomers (804.8-805.3 Da), in FIG. 2E the extracted negative ion current (XIC) chromatogram adjusted to the fragment ion m/z=675 of Disorazole Z and Z-isomers (674.7-675.2 Da), in FIGS. 2F and G the UV spectra of a Z-isomer and of Disorazole Z, in FIGS. 2H and I the MS spectra (ESI, positive mode) of an Z-isomer and of Disorazole Z, with m/z 747 as the $[M+H]^+$ molecular ion, m/z 764=746+18 as $[M+NH_4]^+$ ion, and m/z 769=746+23 as the $[M+Na]^+$ ion, in FIGS. 2J and K the MS spectra (ESI, negative mode) of a Z-isomer and of Disorazole Z, with m/z 805=746+59 as the $[M+AcO^-]^-$ molecular ion cluster, and a fragment at m/z 675=746−H−70 ($=C_4H_6O$)=$C_{36}H_{39}N_2O_{11}$ as the [M−H−side chain]$^-$ ion.

In the examples, percentages are weight per volume, unless specified otherwise.

EXAMPLE 1

Disorazole Z

As an example for the novel compounds comprising the cyclic 25-membered core structure, Disorazole Z is analyzed, carrying identical substituents on carbon atoms C13 and C13' of general structure IV, which carbon atoms are numbered 25 and 33 of following formula IX', respectively. From NMR in acetone-D6 (600/150 MHz, acetone at 2.05/29.80 ppm), the data of table 1 were obtained.

TABLE 1

NMR data for Disorazole Z in acetone-D6:

| | m | J | C | $\delta_c$ | m |
|---|---|---|---|---|---|
| — | — | — | 1, 13 | 162.35 | s |
| — | — | — | 2, 14 | 135.72 | s |
| 8.53 | s | — | 3, 15 | 145.05 | d |
| — | — | — | 4, 16 | 159.65 | s |
| 6.19 | d | 15.5 | 5, 17 | 116.49 | d |
| 6.81 | m | *) | 6, 18 | 137.66 | d |
| 6.16 | dd | 11.1, 14.9 | 7, 19 | 131.81 | d |
| 6.78 | dd | 11.5, 14.9 | 8, 20 | 134.99 | d |
| 6.11 | t | 11.1 | 9, 21 | 132.78 | d |
| 5.69 | m | — | 10, 22 | 131.08 | d |
| 2.69 ($H_a$) | m | — | 11, 23 | 30.24 | t |
| 2.66 ($H_b$) | m | — | | | |
| 5.45 | dd | 2.1, 9.2 | 12, 24 | 76.16 | d |
| — | — | — | 25, 33 | 56.13 | s |
| 4.44 | t | 6.2 | 26, 34 | 75.53 | d |
| 5.65 | m | — | 27, 35 | 131.57 | d |
| 5.74 | dq | 15.4, 6.2 | 28, 36 | 128.72 | d |
| 1.70 | dd | 1.1, 6.4 | 29, 37 | 17.93 | q |
| 1.36 | s | — | 30, 38 | 13.53 | q |
| — | — | — | 31, 39 | 173.81 | s |

TABLE 1-continued

NMR data for Disorazole Z in acetone-D6:

| | m | J | C | $\delta_c$ | m |
|---|---|---|---|---|---|
| 3.61 | s | — | 32, 40 | 51.85 | q |
| 4.16 | d | 4.9 | 26/34-OH | — | — |

*) breites Signal, überlappend mit 8-H; in CDCl$_3$: 7-H: 6.74(dd(br), 11.6, 15.2Hz), 8-H: 6.59(dd, 11.8, 14.4Hz)

From the analytical data, the following structural formula for Disorazole Z is deduced, wherein numbers denote carbon atoms unless otherwise specified:

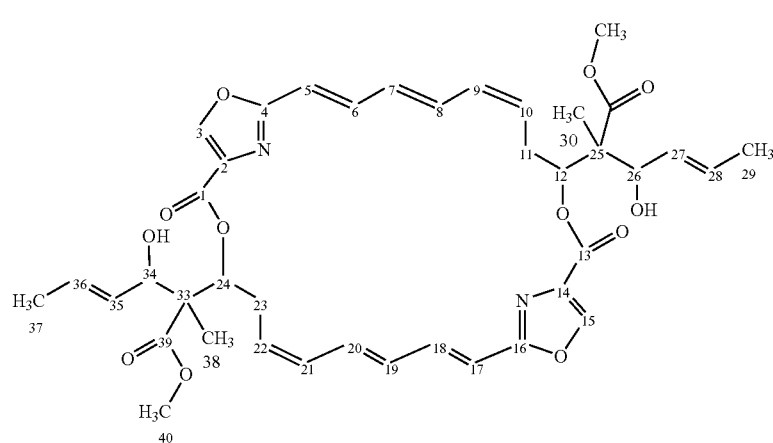

IX'

For Disorazole Z, a formula of $C_{40}H_{46}N_2O_{12}$ at M=746.80 has been determined, calculated as 746.30507 Da, determined to 746.3037 Da in FAB-MS (using a matrix of 3-NBA).

EXAMPLE 2

Biological Activities of Disorazole Z

As an example for compounds according to the invention, Disorazole Z has been analyzed for biological activity following the methods as disclosed in Irschik et al. (The Sorangicins, novel and powerful inhibitors of eubacterial RNA polymerase isolated from myxobacteria, J. Antibiotics 40: 7-13 (1987)). The following minimal inhibitory concentrations against organisms were found:

TABLE 2

Minimal inhibitory concentrations (MIC) against micro-organisms

| Tested micro-organism | MIC (µg/mL) |
|---|---|
| Mucor hiemalis | >6 |
| Botrytis cinerea | 6 |
| Pythium debaryanum | 3 |
| Rhodotorula glutinis | 3 |
| Saccharomyces cerevisiae | >6 |
| Staphylococcus aureus | >25 |
| Escherichia coli (DMSZ 5347) | >25 |

The toxicity tested against the mouse fibroblast cell line L929 (ATCC CCL 1) according to Sasse et al. (J. Antibiotics 56:827-831 (2003)), an inhibitory concentration $IC_{50}$ of 30 pg/mL was determined.

EXAMPLE 3

Producing the Compound by Fermentation

As an example for the production of the compounds according to the present invention, Disorazole Z was produced by fermentation of *Sorangium cellulosum*.

With the present disclosure of the novel compound at hand, producer strains, e.g. myxobacteria can be identified by persons skilled in the art. As an example, *Sorangium cellulosum* strain Soce 1875 (available at DSMZ under accession No. DSM53600), which is a producer strain of Disorazole Z and, concurrently, of Disorazole Z-epoxide, was cultivated in shake flasks.

Analysis of Disorazole Z and of Disorazole Z-epoxide was by HPLC-MS using an HP 1100 system equipped with a solvent gradient system [automatic injector, column oven (40° C.), DAD-UV-detector; column Nucleodur 100-5 C18 EC, 125/2 mm (Macherey-Nagel); solvent A=water with 5% acetonitrile, B=acetonitrile with 5% water, each with ammonium acetate buffer (0.5 mM) adjusted to pH 5.5 with 30 µL/L acetic acid; gradient: 10% B increasing to 100% B in 30 min, 10 min 100% B; flow rate 0.3 mL/min]. Mass spectra were recorded in the positive-negative switching mode on a PE SCIEX API 2000 LC/MS/MS system with an ion spray ionization interface.

EXAMPLE 4

Fermentation of *Sorangium cellulosum* for Production of Disorazole Z and/or Diorazole Z-epoxide For fermentative production of Disorazole Z and/or Disorazole Z-epoxide, depending on the specific producer strain of *Sorangium*, a starting culture cultivated in shake flasks is preferred for inoculation of a fermenter. The fermentation process is carried out for example as batch or fed-batch.

For the starting culture, a medium was used comprising 0.8% soluble starch (Merck 1.01252), 0.2% yeast extract, 0.2% degreased soy meal, 0.1% $CaCl_2 \times 2H_2O$, 0.1% $MgSO_4 \times 7H_2O$, 8 mg/L Na—Fe-EDTA, 1% HEPES buffer, 0.2% glucose, 1% XAD resin at a pH of 7.4 at the start of the cultivation. For the starting culture, shake flasks can be incubated at 30° C. at an agitation of 160 rpm. For fermentation, a batch fermentation of 70 liters of medium identical to that for the starting culture but without HEPES buffer at a pH of 7.9 before autoclaving was used.

For adsorption of Disorazole Z and/or Disorazole Z-epoxide, 1% (vol/vol) XAD (Amberlite XAD 16, Rohm and Haas) was added.

The fermenter was inoculated with one liter starting culture, cultivation was at a temperature of 30° C., aeration at 5.5 L/min at a stirrer speed of 80 rpm. If necessary, the pH was kept constant at or above 6.8 by addition of 5% KOH solution during the course of the fermentation. Residual starch was controlled by the iodine reaction and the glucose concentration was monitored, e.g. using test stripes (Roche). The course of the fermentation is shown in FIG. 1, depicting the course of dissolved oxygen tension ($pO_2$), the pH and the stirrer speed.

Substrate and product concentrations were as follows:

| Day of fermentation | glucose | starch (iodine reaction) | conc. of Disorazole Z (μg/mL) |
|---|---|---|---|
| 10 | trace | blue | 55 |
| 11 | 0 | blue | 92 |
| 12 | 0 | light blue | 96 |

The production culture is ready for harvesting when glucose and starch are essentially metabolized and when the concentration of Disorazole Z reaches a plateau. After a total of twelve days, the fermentation was stopped and harvested by collecting the XAD resin by sieving. Cells which are attached to the XAD are included in the subsequent extraction and purification steps.

For the production of compounds wherein the lactonization is arranged between C14 and C1' and/or between C14' and C1 instead of C12 and C1' and C12' and C1, as well as for compounds having alternative configurations of double bonds and varying substituents, the duration of the fermentation was extended by 2 to 8 days, optionally decreasing the cultivation temperature to about 20-22° C., preferably omitting the adsorbing resin (XAD).

For analytical purposes, an aliquot from the fermentation culture was used for collection of XAD resin and cell mass, followed by extractions using methanol, methanol: ethanol: isopropanol (80:15:5), and a final step using acetone. The extracts are combined, concentrated and analysed in HPLC-MS.

When using an alternative *Sorangium cellulosum* strain, preferably Soce 427, listed at DSMZ under accession number DSM53419, the following medium can be used for the starting culture: 0.3% starch (Cerestar SF 12618, Cerestar Deutschland, Krefeld), 0.2% degreased soy meal (Soyamine 50 T, Lucas Meyer, Hamburg), 0.1% yeast extract (Marcor), 0.1% magnesium sulfate (Roth, P027.2), 0.05% calcium chloride (Merck, 1.02382), 8 mg/L sodium-iron salt of ethylenediaminetetraacetic acid (Na—Fe-EDTA) (Merck, 108413) and 0.9% HEPES buffer (Roth, 9105.3), at a pH at 7.5. After autoclaving, 20% glucose solution (Riedel-de Haën 16301) was added to a final of 0.3% glucose. For fermentation, the same medium except for HEPES buffer was used at a pH of 7.9 before autoclaving.

EXAMPLE 5

Isolation of Disorazole Z from Fermentation Broth

Following a fermentation according to Example 4, wet cell mass and XAD resin collected by centrifugation of 70 L fermentation broth of *Sorangium cellulosum*, strain So ce427, was extracted with portions of 3 L of methanol. The combined filtrate was evaporated to give a residual aqueous mixture. If necessary, water was added to give 1.2-1.5 L which was extracted with three portions of 1.2 L dichloromethane. The combined organic solutions were dried with anhydrous sodium sulfate and then evaporated to dryness. The residue was redissolved in 1 L of aqueous methanol (97%) and partitioned with three portions of heptane. The methanol layer was evaporated, diluted with toluene and evaporated to dryness. The residue of 14 g was separated by gel chromatography with methanol on Sephadex LH-20 (Pharmacia) to give an enriched fraction of about 9 g, which was purified by RP-MPLC (ODS-AQ, 120 Å, S 16 μm) with methanol-water (65/35) to give 4.2 g of Disorazol Z.

The invention claimed is:
1. A compound comprising:
a structure according to Formula II:

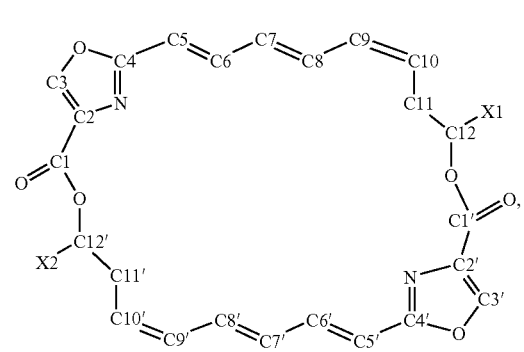

wherein carbon atom C5 is substituted with R4, carbon atom C6 is substituted with R6, carbon atom C7 is substituted with R8, carbon atom C8 is substituted with R10, carbon atom C9 is substituted with R12, carbon atom C10 is substituted with R14, carbon atom C11 is substituted with R16, carbon atom C12 is substituted with X1, carbon atom C5' is substituted with R18, carbon atom C6' is substituted with R20, carbon atom C7' is substituted with R22, carbon atom C8' is substituted with R24, carbon atom C9' is substituted with R26, carbon atom C10' is substituted with R28, carbon atom C11' is substituted with R30 and carbon atom C12' is substituted with X2;

wherein substituents R4, R6, R8, R10, R12, R14, R16, R18, R10, R22, R24, R26, R28 and R30 are each hydrogen;

wherein X1 and X2 are, independently, selected from the group consisting of hydrogen, alkyl, cycloalkyl, cycloalkylalkyl, alkenyl, alkynyl, aryl, heteroaryl, arylalkyl, heteroarylalkyl, heterocyclyl, heterocyclylalkyl, alkylsulfonyl, arylsulfonyl, arylalkylsulfonyl, carbonyl, acetyl, alkoxyl, aryloxyl, arylalkyloxyl, mono-alkylamino, di-alkylamino, alkylcyano, disulfidylalkyl, and alkylsulfidyl substituents;

wherein X1 and X2 are further substituted in their alkyl, cycloalkyl, alkenyl, alkynyl, aryl, heteroaryl, arylalkyl, heteroarylalkyl, heterocyclyl, heterocyclylalkyl, alkylsulfonyl, arylsulfonyl, arylalkylsulfonyl, carbonyl, acetyl, alkoxyl, aryloxyl, arylalkyloxyl, mono-alkylamino, di-alkylamino, alkylcyano, disulfidylalkyl, and/or alkylsulfidyl groups by 1, 2 or 3 substituents independently selected from the group consisting of alkyl, cycloalkyl, cycloalkylalkyl, alkenyl, alkynyl, aryl, heteroaryl, arylalkyl, heteroarylalkyl, heterocyclyl, heterocyclylalkyl, arylsulfonyl, arylalkylsulfonyl, halogen, fluoro, chloro, bromo, iodo, —N$_3$, NO$_2$, =O, =S, —S(O)$_2$, hydroxyl, carbonyl, acetyl, alkoxyl, aryloxyl, arylalkyloxyl, amino, imino, hydroxylamino, mono-alkylamino, di-alkylamino, hydrazinyl, cyano, alkylcyano, sulfhydryl, disulfidylalkyl and sulfatidyl; and wherein said alkyl groups have 1 to 12 carbon atoms; said cycloalkyl groups have 3 to 30 carbon atoms; said cycloalkyl contains 1 to 3 rings; said alkenyl group includes from 2 to 12 carbon atoms; said alkynyl group includes from 2 to 12 carbon atoms; said aryl group includes 3 to 14 carbon atoms; said heteroaryl group includes a 5-, 6- or 7-membered cyclic aromatic having from 1 to 5 first heteroatoms, each first heteroatom being independently selected from the group consisting of nitrogen, oxygen and sulfur; and said heterocyclyl includes 3 to 14 carbon atoms and from 1 to 5 second heteroatoms, at least 5 of said carbon atoms forming a non-aromatic ring, said second heteroatoms being independently selected from the group consisting of nitrogen, oxygen and sulfur.

2. The compound of claim 1 wherein the structure of Formula II further comprises an epoxide group as shown in the structure of Formula IV:

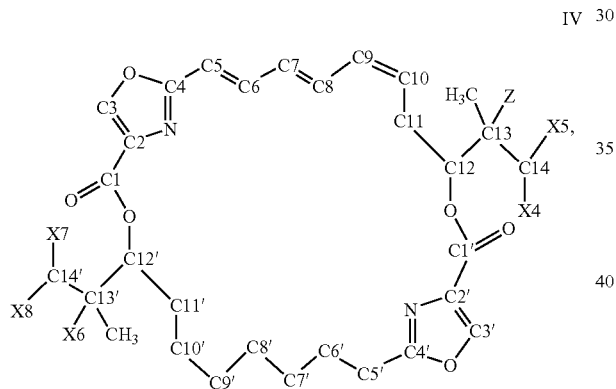

and wherein X3, X4, X5, X6, X7 and X8 are, independently, selected from the group consisting of alkyl, cycloalkyl, cycloalkylalkyl, alkenyl, alkynyl, aryl, heteroaryl, arylalkyl, heteroarylalkyl, heterocyclyl, heterocyclylalkyl, alkylsulfonyl, arylsulfonyl, arylalkylsulfonyl, carbonyl, acetyl, alkoxyl, aryloxyl, arylalkyloxyl, mono-alkylamino, di-alkylamino, alkylcyano, disulfidylalkyl, and alkylsulfidyl substituents.

3. The compound of claim 1 wherein X1 and X2 are, independently, selected from the group consisting of one of the following formulae:

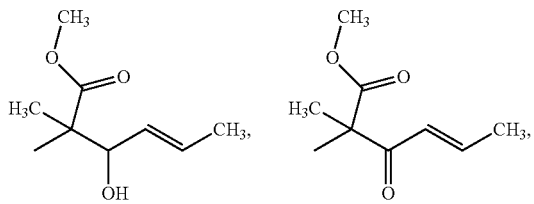

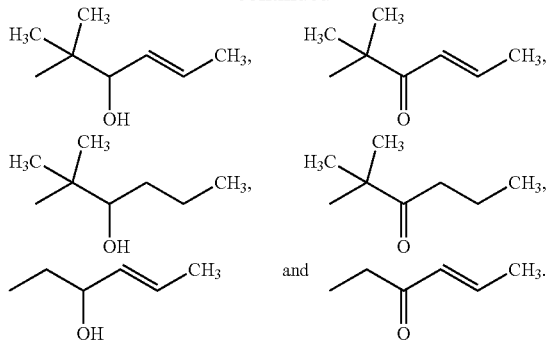

4. A compound comprising:
a structure according to Formula VIII:

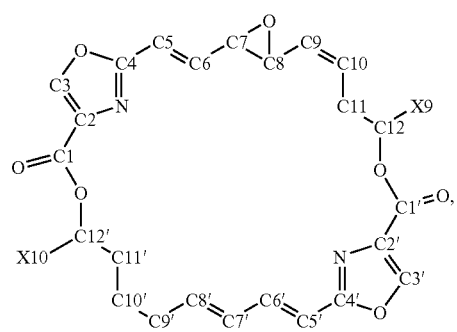

wherein carbon atom C5 is substituted with R4, carbon atom C6 is substituted with R6, carbon atom C9 is substituted with R12, carbon atom C10 is substituted with R14, carbon atom C11 is substituted with R16, carbon atom C12 is substituted with X1, carbon atom C5' is substituted with R18, carbon atom C6' is substituted with R20, carbon atom C7' is substituted with R22, carbon atom C8' is substituted with R24, carbon atom C9' is substituted with R26, carbon atom C10' is substituted with R28, carbon atom C11' is substituted with R30 and carbon atom C12' is substituted with X2;

wherein substituents R4, R6, R12, R14, R16, R18, R10, R22, R24, R26, R28 and R30 are each hydrogen;

wherein X9 and X10 are, independently, selected from the group consisting of hydrogen, alkyl, cycloalkyl, cycloalkylalkyl, alkenyl, alkynyl, aryl, heteroaryl, arylalkyl, heteroarylalkyl, heterocyclyl, heterocyclylalkyl, alkylsulfonyl, arylsulfonyl, arylalkylsulfonyl, carbonyl, acetyl, alkoxyl, aryloxyl, arylalkyloxyl, mono-alkylamino, di-alkylamino, alkylcyano, disulfidylalkyl, and alkylsulfidyl substituents;

wherein X9 and X10 are further substituted in their alkyl, cycloalkyl, cycloalkylalkyl, alkenyl, alkynyl, aryl, heteroaryl, arylalkyl, heteroarylalkyl, heterocyclyl, heterocyclylalkyl, alkylsulfonyl, arylsulfonyl, arylalkylsulfonyl, carbonyl, acetyl, alkoxyl, aryloxyl, arylalkyloxyl, mono-alkylamino, di-alkylamino, alkylcyano, disulfidylalkyl, and/or alkylsulfidyl groups by 1, 2 or 3 substituents independently selected from the group consisting of alkyl, cycloalkyl, cycloalkylalkyl, alkenyl, alkynyl, aryl, heteroaryl, arylalkyl, heteroarylalkyl, heterocyclyl, heterocyclylalkyl, alkylsulfonyl, arylsulfonyl, arylalkylsulfonyl, halogen, fluoro, chloro, bromo, iodo, —N₃, NO₂, ═O, ═S, ═S(O)₂, hydroxyl, carbonyl, acetyl, alkoxyl, aryloxyl, arylalkyloxyl, amino, imino, hydroxylamino, mono-alkylamino, di-alkylamino, hydrazinyl, cyano, alkylcyano, sulfhydryl, disulfidylalkyl and sulfatidyl; and wherein alkyl groups have 1 to 12 carbon atoms; cycloalkyl groups have 3 to 30 carbon atoms; said cycloalkyl contains 1 to 3 rings; said alkenyl group includes from 2 to 12 carbon atoms; said alkynyl group includes from 2 to 12 carbon atoms; said aryl group includes 3 to 14 carbon atoms; said heteroaryl group includes a 5-, 6- or 7-membered cyclic aromatic having from 1 to 5 first heteroatoms, each first heteroatom being independently selected from the group consisting of nitrogen, oxygen and sulfur; and said heterocyclyl includes 3 to 14 carbon atoms and from 1 to 5 second heteroatoms, at least 5 of said carbon atoms forming a non-aromatic ring, said second heteroatoms being independently selected from the group consisting of nitrogen, oxygen and sulfur.

5. The compound of claim 4 wherein the structure of Formula VII further comprises an epoxide as shown in the structure of Formula VI:

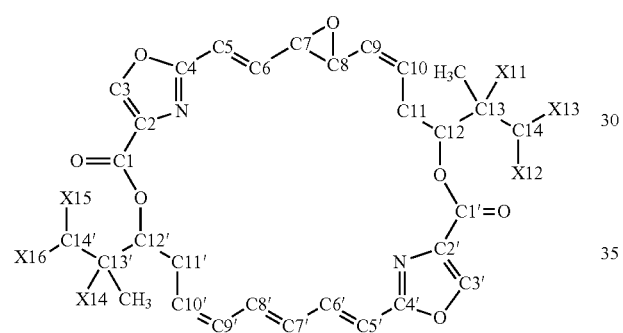

VI wherein X11, X12, X13, X14, X15 and X16 are, independently, selected from the group consisting of alkyl, cycloalkyl, cycloalkylalkyl, alkenyl, alkynyl, aryl, heteroaryl, arylalkyl, heteroarylalkyl, heterocyclyl, heterocyclylalkyl, alkylsulfonyl, arylsulfonyl, arylalkylsulfonyl, carbonyl, acetyl, alkoxyl, aryloxyl, arylalkyloxyl, mono-alkylamino, di-alkylamino, alkylcyano, disulfidylalkyl, and alkylsulfidyl substituents.

6. The compound of claim 5 wherein X9 and X10 are, independently, selected from the group consisting of one of the following formulae:

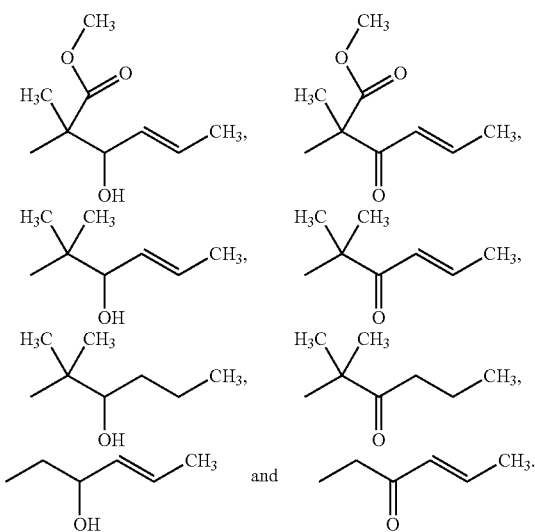

and

7. A process of producing a compound comprising:
creating a fermentation broth using a myxobacterial strain of the genus *Sorangium* at a temperature of 20 to 32° C. under aeration for 8 to 20 days;
isolating the compound of claim 1 from the fermentation broth; and
purifying the compound.

8. A process of producing a compound comprising:
creating a fermentation broth using a myxobacterial strain of the genus *Sorangium* at a temperature of 20 to 32° C. under aeration for 8 to 20 days;
isolating the compound of claim 1 from the fermentation broth; and
purifying the compound.

9. The process of claim 8 wherein said myxobacterial strain is *Sorangium cellulosum*.

10. The process of claim 8 wherein said myxobacterial strain is *Sorangium cellulosum*.

11. A pharmaceutical composition comprising the compound of claim 1 or a pharmaceutically acceptable salt thereof.

12. A pharmaceutical composition comprising the compound of claim 5 or a pharmaceutically acceptable salt thereof.

* * * * *

UNITED STATES PATENT AND TRADEMARK OFFICE
CERTIFICATE OF CORRECTION

PATENT NO. : 7,947,719 B2  Page 1 of 1
APPLICATION NO. : 11/486140
DATED : May 24, 2011
INVENTOR(S) : Irschik et al.

It is certified that error appears in the above-identified patent and that said Letters Patent is hereby corrected as shown below:

In the Claims:

Col. 21, lines 20-21   Please delete "Formula VII," and insert --Formula VIII-- therefor.
Claim 5

Signed and Sealed this
Fifth Day of June, 2012

David J. Kappos
*Director of the United States Patent and Trademark Office*